United States Patent [19]

Browning

[11] Patent Number: 5,141,963
[45] Date of Patent: * Aug. 25, 1992

[54] METHOD OF CONTROLLING TICKS AND OTHER INSECT PESTS

[76] Inventor: Henry A. Browning, Rte. 1, Box 90, Quitman, Ga. 31643

[*] Notice: The portion of the term of this patent subsequent to Jun. 25, 2008 has been disclaimed.

[21] Appl. No.: 719,014

[22] Filed: Jun. 21, 1991

Related U.S. Application Data

[60] Division of Ser. No. 459,273, Dec. 29, 1989, Pat. No. 5,026,734, which is a continuation-in-part of Ser. No. 297,185, Jan. 12, 1989, abandoned.

[51] Int. Cl.⁵ .................... A01N 31/14; A01N 25/34
[52] U.S. Cl. .................... 514/723; 514/919; 424/411
[58] Field of Search ............... 514/723, 919; 424/411

[56] References Cited

U.S. PATENT DOCUMENTS

| | | | |
|---|---|---|---|
| 3,930,010 | 12/1978 | Klopping | 514/388 |
| 3,930,030 | 12/1975 | Klopping | 514/338 |
| 3,984,570 | 10/1976 | Bent et al. | 514/723 |
| 4,212,870 | 7/1980 | Gibbs | 546/304 |
| 4,227,911 | 10/1980 | Leonard et al. | 71/77 |
| 4,497,831 | 2/1985 | Lover et al. | 514/717 |

FOREIGN PATENT DOCUMENTS 1604859 12/1981 United Kingdom.

OTHER PUBLICATIONS

Tergitol Publications: Overview and Product Information, Specialty Nonionic Surfactants, Nontonic Surfactants: 15-S-9, 15-S-3, 15-S-5, 15-S-7, 15-S-20, 15-S-30 and 15-S-40.

*Primary Examiner*—Allen J. Robinson
*Attorney, Agent, or Firm*—Dowell & Dowell

[57] ABSTRACT

This invention relates to the discovery that a very particular kind of nonionic surfactant, namely an alkyloxypolyethyleneoxyethanol can be used as the sole active ingredient to control ticks and other insect pests. It is believed that these alkyloxypolyethyleneoxyethanols can be represented by the formula:

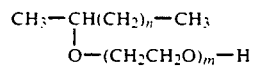

wherein n is from 9 to 15 and m is from 3 to 40.

10 Claims, No Drawings

METHOD OF CONTROLLING TICKS AND OTHER INSECT PESTS

CROSS-REFERENCE TO RELATED APPLICATIONS

This application is a divisional application of Ser. No. 07/459,273 filed Dec. 29, 1989 now U.S. Pat. No. 5,026,734 issued Jan. 25, 1991, which is a continuation-in-part application of Ser. No. 07/297,185 filed Jan. 12, 1989, now abandoned.

BACKGROUND OF THE INVENTION

Most people have experienced the discomfort and aggravation of insects such as ticks, mosquitoes, and chiggers. Numerous repellents have been marketed for both area spraying as well as personal application to attempt to prevent such insects from attacking human beings as a source of food supply. However, the effectiveness of most repellents and related insecticides has been limited and their use in some environments may be potentially hazardous to people's health either by direct skin contact or respiratory irritation. Additionally, some such insects are known to carry potentially fatal diseases such as Lyme's disease which is carried or transmittal by the deer ticks indigenous to many areas of the United States or Rocky Mountain spotted fever carried or transmitted by other ticks.

In some industries, such as in the forestry or timber business, workers must be protected from exposure to potentially dangerous and even life-threatening insects. Special clothes have been designed to protect workers by insuring that maximum body coverage is provided and chemical repellents may be directly applied or used to treat clothing. However, totally successful repellents have not been previously available.

SUMMARY OF THE INVENTION

This invention relates to the discovery that a very particular kind of nonionic surfactant, namely an alkyloxypolyethyleneoxyethanol can be used as the sole active ingredient to control mosquitoes, ticks, chiggers and other biting insects. It is believed that these alkyloxypolyethyleneoxyethanols can be represented by the formula:

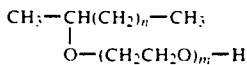

wherein n is from 9 to 15 and m is from 3 to 40.

DESCRIPTION OF THE PREFERRED EMBODIMENT

The aforementioned alkyloxypolyethyleneoxyethanols are biodegradable nonionic surfactants consisting of a mixture of ethoxylates of secondary alcohols having from 9 to 15 carbon atoms in the aliphatic hydrophobic chain, and which have an average of 3 to 5, 7, 9, 12, 15, 20, 30 or 40 moles of ethylene oxide, respectively in the hydrophillic entity. Materials which correspond to the compositions are available commercially as TERGITOL 15-S series of ethylene oxide derivatives manufactured by Union Carbide Corporation (i.e. 15-S-3, 15-S-5, 15-S-7, 15-S-9, 15-S-12, and 15-S-15.) One method for the manufacture of such nonionic surface active agents is believed to be set forth in U.S. Pat. No. 2,870,220 of Union Carbide. A blend or combination of these secondary alcohol ethoxylates such as TERGITOL 15-S-3 added to TERGITOL 15-S-9 results in clear, easily handled materials for application. Of the available ethoxylates of secondary alcohols, TERGITOL 15-S-9 is preferred. As indicated above, it is understood that these nonionic surfactants can be represented by the formula:

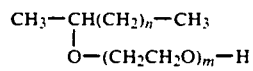

where n is from 9 to 15 and m is from 3 to 40.

Union Carbide characterizes its above TERGITOLS with the empirical formula:

in its Material Safety Data sheets.

The above nonionic surfactants in the same instances can be applied to targets in technical strength if desired. However, because of the active nature of the secondary alcohol ethoxylates, it is recommended that they be admixed with a suitable carrier, this is especially true when applied to targets such as clothing. A suitable inexpensive carrier that is preferred is water. Other more expensive carriers can also be used. In accordance with my invention, the above nonionic surfactants are diluted in water or other carrier and then applied to an individual's clothing, such as by spraying. Other techniques of applying the diluted mixture may be used. The amount of water used as the carrier can vary considerably. Some oils, including vegetable oils, may be used as carriers. Oils are capable of forming a much finer mist than is possible with water and therefore a substantially less volume of oil can be used with the surfactant compared to the same amount of surfactant in water.

The following examples are presented for the purpose of further illustrating and explaining the present invention and are not to be taken as limiting in any regard.

EXAMPLE 1

| TERGITOL 15-S-9 | 1 tbsp (tablespoon) |
|---|---|
| Water | 1 pint |

This solution was sprayed on the clothing of approximately twenty men working in forested areas of Georgia during the time of year when ticks are prevalent. The solution was applied once daily before the men entered the wooded area. After days and weeks of exposure not one worker had a tick anywhere on their persons or clothing. It is believed that the solution exhibited repellant properties discouraging ticks from landing on clothing although it is possible that the solution in some instances exhibited an insecticidal affect on the ticks.

EXAMPLE 2

| TERGITOL 15-S-9 | 1.0 oz. |
|---|---|
| Water | 5-20.0 gallons |

This solution was used as a "bath" for a dog which had been in contact with ticks and fleas found in hunting areas in south Georgia. After being placed in the bath container for a period of several minutes, no parasitic insects were found on the dog.

EXAMPLE 3

| TERGITOL 15-S-9 | 2.0 oz. |
|---|---|
| Water | 15.0 gallons (minimum) |

This solution was sprayed around shrubs and ornamental flowers of a south Georgia residence, where mosquitoes were present in large numbers. Spraying resulted in killing of the pests, with no reinfestation for a period of three days. Stronger solutions of TERGITOL may result in leaf damage.

EXAMPLE 4

| TERGITOL 15-S-9 | 2.0–6.0 oz. (maximum) |
|---|---|
| Water | 15.0 gallons |

TERGITOL 15-S-9 was mixed in solution with the water and sprayed to clothing of individuals exposed to mosquitoes in an area in south Georgia, U.S.A. Once sprayed, no further mosquitoes were noted in the vicinity of those sprayed. A similar application of sprayed solution to clothing prevented chiggers from biting in an area where such insects were present prior to the application of the solution.

Although my invention has been described in connection with the above examples, it is not limited by these examples and should be construed in connection with the following claims and obvious equivalents thereof. For instance, TERGITOL 15-S-3, 15-S-7, 15-S-12 and 15-S-15 have been used for similar applications and the same rates as set forth in the examples in water and/or oil solutions with similar results being achieved. Therefore, it is believed that the nonionic surfactants of the TERGITOL-15-S series are believed to fall within the scope of the present invention.

I claim:

1. A method for controlling ticks, mosquitoes, and other insect pests which comprises applying to the location thereof a solution including a liquid carrier and at least one nonionic surfactant represented by the formula:

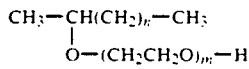

where n is from 9–15 and m is from 3–40 and wherein the surfactant is present in an amount of at least one ounce per twenty gallons of carrier.

2. The method defined in claim 1 wherein said solution is sprayed on clothing of an individual prior to being exposed to the insect pests.

3. The method defined in claim 2 wherein said liquid carrier is water.

4. The method defined in claim 2 in which said surfactant is present in an amount equivalent to at least 1 tbsp per pint with water as said carrier.

5. The method defined in claim 1 in which said surfactant is present in an amount equivalent to between 2 to 6 ounces per 15 gallons of said carrier.

6. A method of treating clothing to repel ticks and other insect pests comprising spraying the clothing with a composition including a liquid carrier and at least one nonionic alkyloxypolyethyleneoxyethanol surfactant represented by the formula:

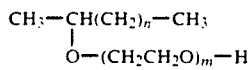

where n is approximately 9–15 and m is from 3–40.

7. The method of claim 6 in which the surfactant is applied in amounts of up to approximately 1 tbsp per pint of water.

8. A method of repelling mosquitoes and other insect pests comprising spraying an area to be treated with a solution including a liquid carrier and at least one nonionic surfactant represented by the formula:

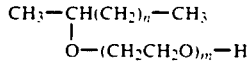

where n is from 9–15 and m is from 3–40.

9. The method of claim 8 wherein the surfactant is applied in solution at a rate of approximately between 2 to 6 ounces per 15 gallons of carrier.

10. The method of claim 8 including the additional steps of spraying the clothing of individuals in the area.

* * * * *